United States Patent [19]

Gerber et al.

[11] Patent Number: 5,087,312
[45] Date of Patent: Feb. 11, 1992

[54] THERMOPILE HAVING REDUCED THERMAL NOISE

[75] Inventors: Martin T. Gerber, Carmel, Ind.; Peter J. Hesketh, Chicago, Ill.

[73] Assignee: Boehringer Mannheim GmbH, Mannheim, Fed. Rep. of Germany

[21] Appl. No.: 551,545

[22] Filed: Jul. 11, 1990

[51] Int. Cl.⁵ ............................................. H01L 35/28
[52] U.S. Cl. .................................. 136/225; 136/224; 136/230; 136/231; 136/212
[58] Field of Search ................ 136/224, 230, 231, 232, 136/225, 233, 212

[56] References Cited

U.S. PATENT DOCUMENTS

| | | | |
|---|---|---|---|
| 3,267,727 | 8/1966 | Benzinger | 73/190 |
| 3,685,344 | 8/1972 | Karle et al. | 73/15 B |
| 4,036,665 | 7/1977 | Barr et al. | 136/202 |
| 4,111,717 | 9/1978 | Baxter | 136/225 |
| 4,779,994 | 10/1988 | Diller et al. | 374/29 |
| 4,935,345 | 6/1990 | Guilbeau et al. | 435/14 |

OTHER PUBLICATIONS

Guilbeau et al., A Potentially Implantable Thermoelectron Sensor, ASAIO, vol. 10, No. 3, pp. 329-335 (Jul. Sep. 87).

Muehlbauer et al., Model for a Thermoelectric Enzyme Glucose Sensor, Anal. Chem., vol. 61, pp. 77-83 (1989).

*Primary Examiner*—Brooks H. Hunt
*Assistant Examiner*—Chrisman D. Carroll
*Attorney, Agent, or Firm*—Felfe & Lynch

[57] ABSTRACT

Thermopile has a plurality of reference junctions and a plurality of measurement thermocouple junctions connected electrically alternately in series on a dielectric support. Each reference junction has thereover a first medium which is nonthermally responsive and each measurement junction has thereover a second medium which is thermally responsive. The first and second mediums occupy areas which are arranged in a checkerboard pattern, the reference junctions under areas occupied by said first medium each being electrically connected directly to a measurement thermocouple under an area occupied by said second medium.

15 Claims, 3 Drawing Sheets

# THERMOPILE HAVING REDUCED THERMAL NOISE

BACKGROUND OF THE INVENTION

The present invention relates to apparatus for measuring very small temperature differences, and more particularly a thermopile for measuring heat generated in a fluid sample while reducing thermal noise due to evaporation or thermal eddies in the sample or surrounding medium.

Such apparatus is used to measure temperature differences produced by an exothermic chemical reaction in close proximity to the thermopile, or by radiating the thermopile with infrared light. The apparatus is especially useful for determining analyte concentration by measuring the heat of reaction when a fluid sample is brought together with a reactive agent such as an enzyme, and provides an attractive alternative to colorimetric methods commonly used for this purpose.

A prior art thermopile of the type shown in FIG. 1 can be obtained as Model 2-142-1 from Barnes Engineering, Newark, CT. Such a thermopile can be used to measure infrared light. The use of a thermopile of similar design to measure the heat produced by a chemical reaction is described by E.J. Guilbeau et al in the ASAIO, Volume 10, No. 3, pages 329-335 (July-Sept. 1987).

Referring to FIG. 1, the prior art thermopile 13 comprises strips of antimony 1 and bismuth 2 which are electrically connected at measurement thermocouple junctions 3 and reference thermocouple junctions 4 but are otherwise separated by electrical insulation 5. Antimony and bismuth are well known for manufacturing thermocouples, and a cumulative voltage $\Delta V$ is developed by the junctions 3, 4 and measured across contact pads 6' by a voltmeter.

In practice, the measurement junctions 3 are covered with a thermally responsive medium, and the reference junctions 4 are covered by a non-thermally responsive medium. For measurement of heat emitted by a body, the hot junctions (measurement thermocouples 3) are covered with black paint to absorb the heat. For measurement of the heat produced by a chemical reaction, the hot junctions are covered by a reagent layer in which a chemical reaction occurs. Such a reaction can be catalyzed by one or more enzymes, which results in an increased production of heat.

As the heat differences measured with these thermopiles are very small, the measurement is very sensitive to heat changes produced by thermal eddies (circulation of media, which has different temperature) or to temperature differences produced by evaporation of a liquid located on the thermopiles. The arrangement of thermopiles used by Muehlbauer et al. allows only the measurement of glucose in a fluid which has a certain linear velocity above the thermopile (M.J. Muehlbauer et al., Anal. Chem. 1989 Vol. 61, pages 77-83). In unstirred fluids a large temperature gradient can be measured between the reference and measurement junctions. A single drop of fluid (e.g. blood or glucose solution) over the thermopile results in a much higher thermal noise due to different evaporation, that means heat loss, over the junctions.

FIGS. 2 and 3 are schematic cross sections of the thermopile of FIG. 1. The antimony and bismuth elements are located on the bottom of a dielectric (electrically insulative) support 7, but for simplicity only the junctions 3, 4 are shown. The thermally responsive medium 8 is placed over the measurement junctions 3, and a drop of sample fluid 15 is applied. A thermally insulative medium 10 isolates the junctions from thermal noise outside the fluid.

FIG. 2 illustrates the case without containment, wherein the sample fluid 15 assumes a convex shape. FIG. 3 approaches this problem by extending the thermal insulation 10 to include sidewalls 11, but the fluid surface then assumes a concave shape. In either case the fluid undergoes a differential evaporation across its surface, which results in the thermal noise discussed above.

Reducing the size of the thermopile can reduce the thermal noise, but does not solve the noise problems attendant the prior art devices to a significant degree.

SUMMARY OF THE INVENTION

Arranging the thermocouples in a checkerboard configuration rather than in groups decreases the thermal noise significantly. More particularly, the thermally responsive medium, whether it is black paint or a heat producing enzyme gel, is arranged in a checkerboard pattern with the hot (measurement) junctions thereunder. Each hot junction is directly connected to a cold (reference) junction under an immediately adjacent area covered by non-thermally responsive medium.

Each area of thermally or non-thermally responsive medium may have but one junction thereunder, or in an alternate embodiment there may be several measurement junctions under an area of thermally responsive medium and there may be several reference junctions under an area of non-thermally responsive medium. In any case the measurement and reference junctions are connected electrically alternately in series and yield a cumulative voltage across the series; this is dictated by the alternation of the antimony and bismuth elements.

A preferred method of manufacturing either the prior art thermopile or the inventive thermopile using nonstandard semiconductor fabrication techniques will be described hereinafter.

Since the type of fixture used to introduce sample fluid to the thermopile can also profoundly affect noise, an inventive test fixture which thermally isolates the thermopile in a glass capillary will also be described. This was used to obtain comparative test results for the prior art thermopile and the inventive thermopile, whereby noise reducing properties of the inventive thermopile were determined. However, it is also possible to reduce noise by using the checkerboard design in an open environment.

DETAILED DESCRIPTION OF THE PREFERRED EMBODIMENT

Figure 4:
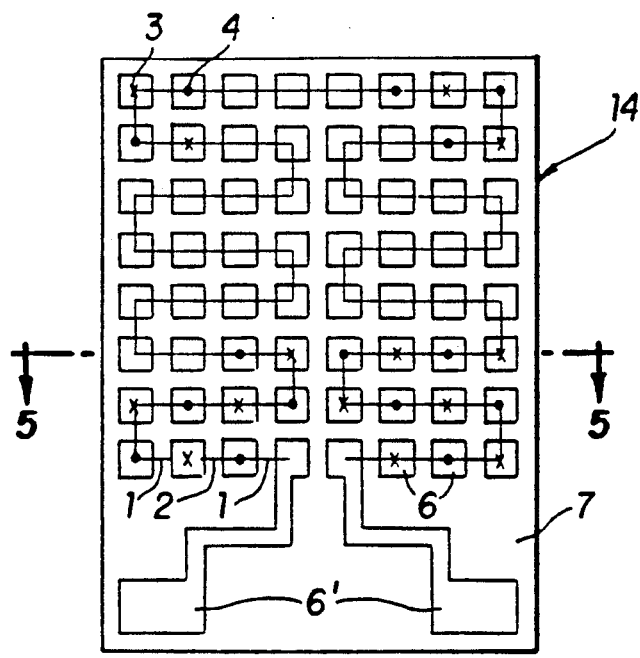
FIG. 4 is a diagrammatic plan view of the thermopile of the present invention.

FIG. 4 illustrates a thermopile 14 according to the invention wherein the measurement junctions 3 are each indicated by an "X" while the reference junctions 4 are each indicated by a solid "O". The thermocouple junctions indicated by X's and O's represent the electrical connection of strips of antimony 1 and bismuth 2, which are well known elements for fabricating thermocouples. The squares 6 represent gold contact pads deposited on an electric insulative (dielectric) substrate 7 according to the preferred method of manufacture; the figure is not drawn to scale and pads 6 are shown relatively quite large. Note that this is a bottom view of the thermopile, and the thermally/non-thermally responsive mediums are not shown.

Figure 5:
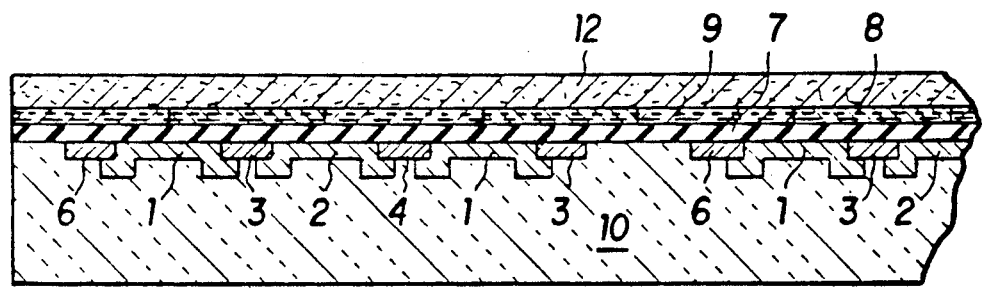
FIG. 5 is a diagrammatic partial cross-section of the thermopile of the present invention.

FIG. 5 is a partial cross section along the line 5—5 of FIG. 4, from which the method of manufacture may be most readily understood. Kapton, a trademark of DuPont for polyimide film, is the preferred material for the dielectric substrate 7 due to its ability to withstand the temperatures of vapor deposition. An extremely thin layer of chromium (not shown) is selectively deposited on the support 7 using shadow masks, the chromium serving as an adhesion layer for ensuing layers of gold and antimony. The gold contact pads 6 and antimony strips 1 are deposited on the chromium using the same shadow masks, and the bismuth strips 2 are then deposited using a further shadow mask. The steps of fabrication, carried out in a class 1000 clean room, are described in greater detail as follows:

(1) Clean 50 μm thick Kapton film by rinsing both sides in acetone and then alcohol. Blow dry in air.

(2) Clamp Kapton film to substrate holder using a metal hoop to spread the Kapton on the support without wrinkles. Inspect and wipe off any visible surface contaminants.

(3) Clean shadow masks by spray rinsing in alcohol several times. Blow dry in hot nitrogen.

(4) Align the shadow mask to the Kapton under the microscope. Clamp on the aluminum hold-down plate which maintains intimate contact between the Kapton and the shadow mask. Mount sample into the vacuum chamber with a glass cover slip. Pump down to $10^{-6}$ torr.

(5) Evaporate 100 to 200 Å of chromium at a rate of 0.3 Å/second, then 0.15 to 0.2 μm of gold at a rate of 1 to 3 Å/second.

(6) Allow vacuum chamber to cool down. This is necessary because any residual hot antimony in the chamber exposed to air will produce a toxic vapor. However, the vapor pressure is negligible at room temperature. Separate shadow mask from Kapton and inspect.

(7) Repeat Steps 4 to 6 for antimony. Evaporate 100 to 200 Å of chromium at a rate of 0.3 to 1.3 Å/second and 0.75 to 0.8 μm of antimony at rate of 200 Å/second.

(8) Repeat Steps 4 through 6 for bismuth. Evaporate 1 to 1.1 μm of bismuth at a rate of 60 Å/second.

(9) Apply heat producing enzyme gel over hot junctions by silk screening (if used to measure reaction heat). Alternatively, gel could be provided overall and then inactivated by UV light over the cold junctions.

(10) Cut off the excess Kapton, measure the impedance of the thermopiles, and cut up the thermopiles as needed.

(11) Mount thermopiles on a glass slide into which holes have been sandblasted for electrical connections.

(12) Attach gold wires with silver epoxy and cure under a heat lamp for 12 hours.

The gold contact pads 6'(FIG. 4) are deposited during deposition of the pads 6 (step 5) and serve as attachment points for the gold wires mentioned at step 11. The glass slide mentioned at step 10 will be described in conjunction with FIG. 6; steps 10-12 are directed to a thermopile intended for use with the test fixture of FIG. 6.

To achieve the cross section of FIG. 5, the checkerboard pattern of active enzyme gel 8 and inactive gel 9 is covered by a layer of filter paper 12, which promotes uniform wetting and in itself reduces the thermal noise resulting from non-uniform evaporation of a drop of sample fluid. By applying enzyme gel over the entire thermopile then inactivating the enzyme in the gel over the cold junctions (step 9), the heat of solution of salts and the like on the gel is uniform over the checkerboard. The side of the dielectric support 7 on which the chromium, gold, antimony and bismuth are deposited is covered by thermal insulation 10 which is preferably a polyurethane foam.

Figure 1:
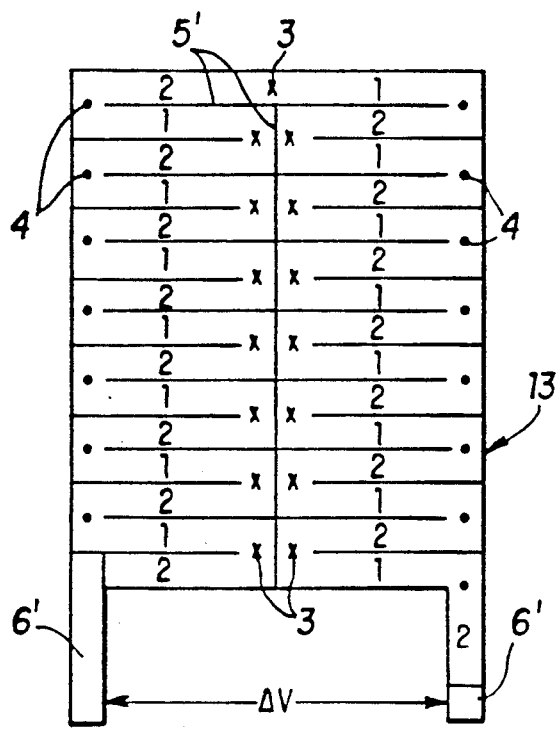
FIG. 1 is a diagrammatic plan view of a prior art thermopile.
Figure 1A:
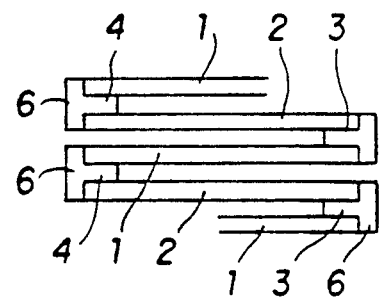
FIG. 1a is a partial diagrammatic plan view showing the individual thermocouple junctions in greater detail.
Figure 2:
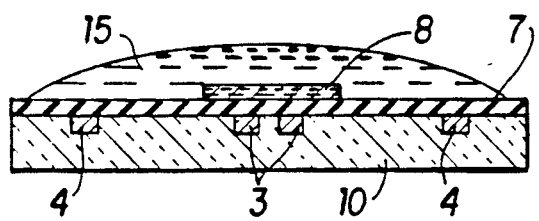
FIG. 2 is a diagrammatic cross-section of a convex drop of sample over the prior art thermopile.
Figure 3:
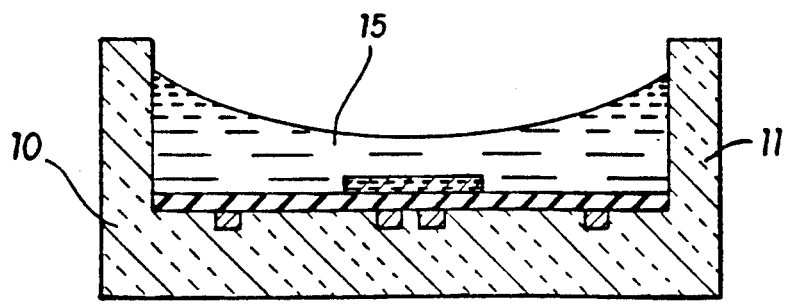
FIG. 3 is a diagrammatic cross-section of a concave drop of fluid over the prior art thermopile.

The above described method of manufacture is also applicable for manufacturing prior art thermopile configurations of which FIG. 1 depicts an example. FIG. 1a shows the gold pads 6 to which the antimony strips 1 and bismuth strips 2 ar connected at junctions 3, 4. The intervening insulation 5 represents areas of the Kapton substrate on which no metals are deposited.

Figure 6:
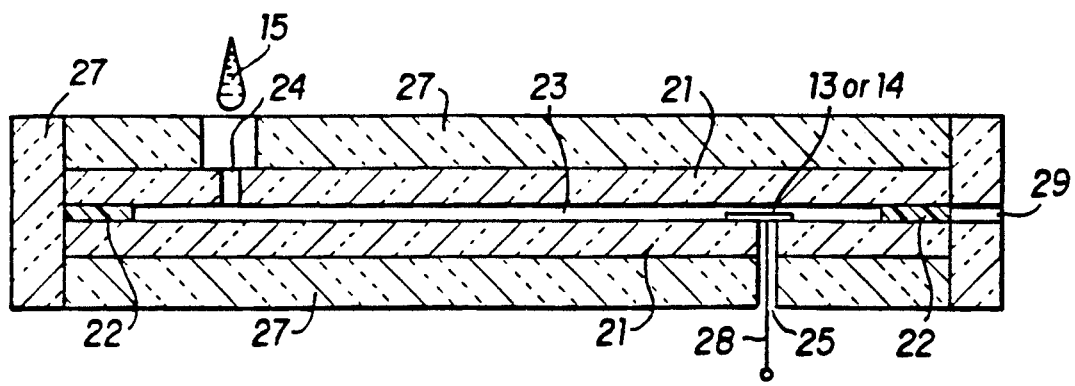
FIG. 6 is a cross-section of a capillary fixture used to test the thermopiles.

FIG. 6 is a cross-section of an apparatus by which comparative test results for the prior art and inventive thermopile layouts were obtained using water as the sample liquid. A pair of glass slides 21 are spaced apart by mylar spacers 22, e.g. Scotch-Tape, to form a capillary 23 therebetween. A sample inlet opening 24 and an electrical access opening 25 are formed in the glass slides 21 by sandblasting. The thermopile 13 or 14 is mounted over opening 25 so that electrical leads 28 attached to pads 6'(FIGS. 1 and 4) may be connected to a voltmeter. The mylar spacers 22 are sandwiched between the plates, and additional sealing can be achieved around the edges of the plates using rubber cement to prevent evaporation. The Kapton substrate actually extends under the mylar spacers 22, but has not been shown for reasons of clarity. This is done to prevent liquid from getting under the thermopile, which in the test embodiment does not have insulation on the junctions. The opening 29 permits evacuation of air as the sample liquid 15 is drawn through passage 23 by capillary action. The test unit is encapsulated in thermal insulation 27.

Figure 7:
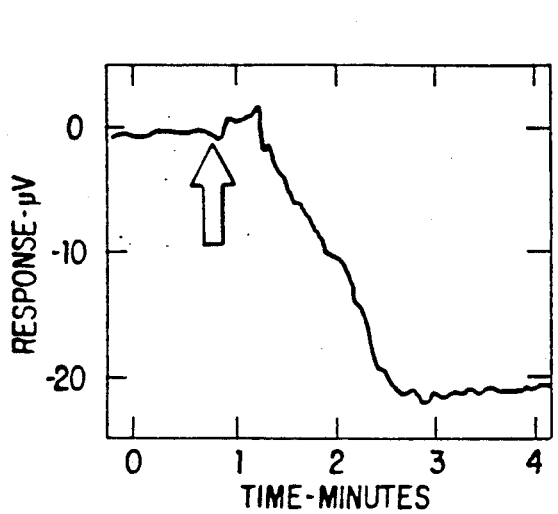
FIG. 7 is a graph of the voltage response of the prior art thermopile in the capillary fixture.
Figure 8:
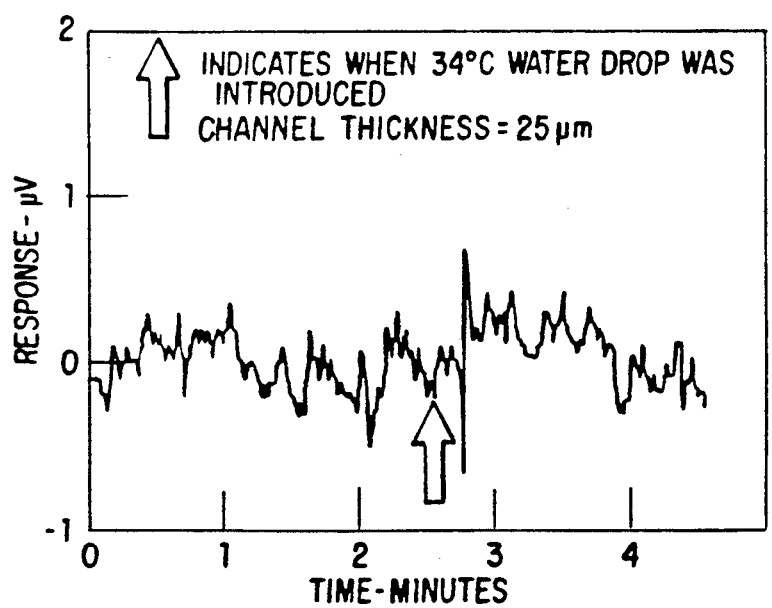
FIG. 8 is a graph of the voltage response of the inventive thermopile in the capillary fixture.

FIGS. 7 and 8 depict the response measured against time, as detected by a Keithley nanovoltmeter connected across thermopiles 13 and 14 of FIGS. 1 and 4 respectively. The response for the chess-board design (FIG. 8) shows only a very short duration transient peak as the sample arrives at the thermopile, then there is no remaining offset. The response for the conventional design (FIG. 7) shows an offset of 20 μV, which contributes significantly to the total noise when the thermopile is used to measure temperature differences due to heat produced by a chemical reaction.

Figure 9:
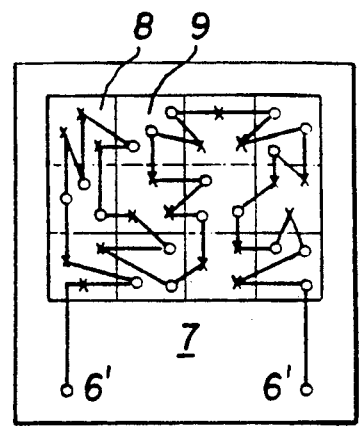
FIG. 9 is a diagrammatic plan view of an alternative embodiment of the present invention.

While the embodiment of inventive thermopile shown in FIG. 4 depicts but one junction under each first (thermally responsive) medium 8 and each second (non-thermally responsive) medium 9, it is also possible to have several junctions under any given area of first or second medium, as shown in the example of FIG. 9. This may be desirable since it is possible to fabricate very fine multiple metal circuitry using photo fabrication techniques, while the checker board pattern of thermally responsive medium reaches a certain dimensional limit where thermal interference with reference junctions under neighboring squares of non-responsive medium can result.

The foregoing is exemplary and not intended to limit the scope of the claims which follow.

What is claimed is:

1. Thermopile apparatus of the type comprising a plurality of reference junctions and a plurality of measurement thermocouple junctions connected electrically alternately in series on a dielectric support, each said measurement junction having thereover a first medium which is thermally responsive, each said reference junction having thereover a second medium which is non-thermally responsive, characterized in that said first and second mediums occupy areas which are arranged in a checkerboard pattern.

2. Thermopile apparatus as in claim 1 wherein each measurement junction under a first medium is electrically connected directly to a reference junction under an immediately adjacent area occupied by said second medium.

3. Thermopile apparatus as in claim 1 wherein said first medium is black, whereby said first medium is thermally responsive to radiation.

4. Thermopile apparatus as in claim 1 wherein said first medium comprises a reagent layer in which an exothermic chemical reaction occurs.

5. Thermopile apparatus as in claim 4 wherein said reagent layer contains at least one enzyme which catalyzes said chemical reaction.

6. Thermopile apparatus as in claim 5 wherein said enzyme comprises glucose oxidase.

7. Thermopile as in claim 6 wherein said enzyme further comprises catalase.

8. Thermopile apparatus as in claim 1 further comprising a capillary action layer on said first and second mediums to uniformly distribute a sample fluid thereover.

9. Thermopile apparatus as in claim 1 wherein said first and second mediums are arranged on the opposite side of said dielectric support from said reference and measurement junctions respectively.

10. Thermopile apparatus as in claim 8 further comprising thermal insulation means on said reference and measurement junctions.

11. Thermopile apparatus as in claim 1 wherein said dielectric support is a polyimide film.

12. Thermopile apparatus as in claim 1 wherein said junctions each comprise an antimony element electrically connected to a bismuth element.

13. Thermopile apparatus as in claim 11 wherein each thermocouple further comprises a gold pad on the dielectric support, said antimony and bismuth elements being electrically connected to said gold pad.

14. Thermopile apparatus as in claim 13 wherein said dielectric support has a layer of chromium, on which said at least said gold pads are deposited, followed by said antimony and bismuth elements.

15. Thermopile apparatus a in claim 1 wherein said first and second mediums comprise a layer of enzyme gel, said enzyme in said gel being inactivated in the areas over said reference junctions.

* * * * *